United States Patent
Knaup et al.

(10) Patent No.: US 11,805,798 B2
(45) Date of Patent: Nov. 7, 2023

(54) PROCESS FOR INCREASING THE STABILITY OF A COMPOSITION COMPRISING POLYUNSATURATED OMEGA-3 FATTY ACIDS

(71) Applicant: Evonik Operations GmbH, Essen (DE)

(72) Inventors: Günter Knaup, Bruchkoebel (DE); Milan Latinovic, Nidda (DE); Michael Schwarm, Alzenau (DE)

(73) Assignee: Evonik Operations GmbH, Essen (DE)

( * ) Notice: Subject to any disclaimer, the term of this patent is extended or adjusted under 35 U.S.C. 154(b) by 246 days.

(21) Appl. No.: 16/947,809

(22) Filed: Aug. 18, 2020

(65) Prior Publication Data
US 2020/0375235 A1 Dec. 3, 2020

Related U.S. Application Data

(62) Division of application No. 15/538,825, filed as application No. PCT/EP2015/080311 on Dec. 17, 2015, now Pat. No. 10,798,962.

(30) Foreign Application Priority Data

Dec. 23, 2014 (EP) .................................. 14199989

(51) Int. Cl.
| | | |
|---|---|---|
| *A61P 29/00* | (2006.01) | |
| *A23L 33/12* | (2016.01) | |
| *A23L 33/115* | (2016.01) | |
| *A23L 33/18* | (2016.01) | |
| *A23L 5/30* | (2016.01) | |
| *A23D 9/02* | (2006.01) | |
| *A61K 9/16* | (2006.01) | |
| *A61K 31/202* | (2006.01) | |
| *A61K 47/18* | (2017.01) | |

(52) U.S. Cl.
CPC ................ *A23L 33/12* (2016.08); *A23D 9/02* (2013.01); *A23L 5/30* (2016.08); *A23L 33/115* (2016.08); *A23L 33/18* (2016.08); *A61K 9/16* (2013.01); *A61K 31/202* (2013.01); *A61K 47/183* (2013.01); *A61K 2300/00* (2013.01)

(58) Field of Classification Search
CPC .. C08K 5/20; C08K 5/101; C08J 3/223; C08J 3/24; C08J 2333/06; C08J 2333/14; C08J 2363/00; C08J 2433/14; C08J 2435/02; C09D 4/06; C09D 7/63; C09D 11/101; C09D 11/102; C09D 11/38; C09D 133/06; C09D 133/14; C09D 7/20; C09D 7/43; C09D 7/80; C09D 163/00; C08F 20/28; C08F 2/44; C08F 2/50
See application file for complete search history.

(56) References Cited

U.S. PATENT DOCUMENTS

| | | | |
|---|---|---|---|
| 2,945,049 | A | 7/1960 | Chang et al. |
| 5,750,572 | A | 5/1998 | Bruzzese |
| 2008/0026109 | A1 | 1/2008 | Abril |
| 2010/0173002 | A1 | 7/2010 | Yulai et al. |
| 2013/0115284 | A1 | 5/2013 | Fujii et al. |

FOREIGN PATENT DOCUMENTS

| | | | |
|---|---|---|---|
| EP | 0 734 373 | | 4/1998 |
| GB | 2 216 522 | | 10/1989 |
| WO | 2007/075632 | | 7/2007 |
| WO | 2008/003064 | | 1/2008 |
| WO | WO-2014011895 | A2 * | 1/2014 ........... A61K 31/202 |

OTHER PUBLICATIONS

International Search Report dated Mar. 7, 2016 in PCT/EP2015/080311 filed Dec. 17, 2015.
Written Opinion dated Mar. 7, 2016 in PCT/EP2015/080311 filed Dec. 17, 2015.
Young Jun Kim, et al., "Total Antioxidant Capacity of Arginine-Conjugated Linoleic Acid (CLA) Complex" Journal of Agricultural and Food Chemistry, vol. 52, No. 3, 2004, XP055172184, pp. 439-444.
Canadian Office Action dated Feb. 6, 2023, in Canadian Application No. 2,969,159, 3 pages.

* cited by examiner

Primary Examiner — Layla Soroush
(74) Attorney, Agent, or Firm — Grüneberg and Myers PLLC

(57) ABSTRACT

A solid product composition includes at least one salt of a cation derived from lysine with an anion derived from a polyunsaturated omega-3 fatty acid. The solid product composition is formed by (i) providing a starting composition containing at least one polyunsaturated omega-3 fatty acid component; (ii) providing a lysine composition; and (iii) admixing an aqueous, an aqueous-alcoholic or an alcoholic solution of starting composition and lysine composition, and subjecting resulting admixture to spray drying conditions subsequently, thus forming the solid product composition containing at least one salt of a cation derived from lysine with an anion derived from a polyunsaturated omega-3 fatty acid.

20 Claims, No Drawings

PROCESS FOR INCREASING THE STABILITY OF A COMPOSITION COMPRISING POLYUNSATURATED OMEGA-3 FATTY ACIDS

CROSS REFERENCE TO RELATED APPLICATIONS

The present application is a divisional of U.S. application Ser. No. 15/538,825, filed on Jun. 22, 2017, which is a § 371 national stage entry application of PCT/EP2015/080311, filed on Dec. 17, 2015, which claims the benefit of European Application No. 14199989.6, filed on Dec. 23, 2014. The content of each of these applications is incorporated by reference herein in its entirety.

Numerous health benefits have been correlated with the supplemental intake of polyunsaturated fatty acids (PUFAs) by an extensive body of evidence gathered over the course of the past several decades. Prevention of cardiovascular disease and reducing the symptoms of inflammatory conditions are amongst the most prominent examples, however, preventing the promotion and progression stages of some types of cancer, reducing blood pressure and blood cholesterol as welt as positive effects in the treatment of depression and schizophrenia, Alzheimer's disease, dyslexia and attention-deficit or hyperactivity disorder, amongst others, have been reported as well. Furthermore, because some PUFAs are considered to be essential for the development of brain, nervous system and eye, nowadays routinely, infant nutrition is supplemented with specific PUFAs.

However, the manufacture of food, nutritional and pharmaceutical products containing PUFAs is impeded by their high susceptibility towards oxidative deterioration. Oxidation has negative, both nutritional and organoleptic, consequences; namely, changes in nutritional value such as the destruction of essential fatty acids; rancidity which produces off-flavors and pronounced odors; color changes such as darkening of fats and oils, as well as flavor toss. Oxidation of PUFAs produces a complex mixture of volatile secondary oxidation products, and these cause particularly objectionable off-flavors.

Three different strategies have been described in the art and applied in industry to stabilize PUFAs against oxidative deterioration (Arab-Tehrany E. et al. Trends in Food Science & Technology 25 (2012)24-33);
addition of antioxidants,
microencapsulation, and
modified atmosphere packaging.

Despite the fact that these strategies offer solutions for a number of oxidation-related problems, new approaches are still needed in order to respond to remaining challenges in current scenarios and potential future settings dictating particular technical and economic boundary conditions.

It was now found that compositions comprising polyunsaturated omega-3 fatty acids can be stabilized against oxidation by a process comprising the following steps:
(i) providing a starting composition comprising at least one polyunsaturated omega-3 fatty acid component.
(ii) providing a lysine compos iron;
(iii) admixing aqueous, aqueous-alcoholic or alcoholic solutions of starting composition and lysine composition, and subjecting resulting admixture to spray drying conditions subsequently, thus forming a solid product composition comprising at least one salt of a cation derived from lysine with an anion derived from a polyunsaturated omega-3 fatty acid; the product composition exhibiting a solvent content SC selected from the following. SC<5 wt %, SC<3 wt %. SC<1 wt %. SC<0.5 wt %.

In the context of tho present invention the term PUFA is used interchangeably with the term polyunsaturated fatty acid and defined as follows: Fatty acids are classified based on the length and saturation characteristics of the carbon chain. Short chain fatty acids have 2 to about 6 carbons and are typically saturated. Medium chain fatty acids have from about 6 to about 14 carbons and are also typically saturated. Long chain fatty acids have from 16 to 24 or more carbons and may be saturated or unsaturated. In longer chain fatty acids there may be one or more points of unsaturation, giving rise to the terms "monounsaturated" and "polyunsaturated," respectively. In the context of the present invention long chain polyunsaturated fatty acids having 20 or more carbon atoms are designated as polyunsaturated fatty acids or PUFAs.

PUFAs are categorized according to the number and position of double bonds in the fatty acids according to well established nomenclature. There are two main series or families of LC-PUFAs, depending on the position of the double bond closest to the methyl end of the fatty acid. The omega-3 series contains a double bond at the third carbon, while the omega-6 series has no double bond until the sixth carbon. Thus, docosahexaenoic acid ("DHA") has a chain length of 22 carbons with 6 double bands beginning with the third carbon from the methyl end and is designated "22:6 n-3" (all-cis-4,7,10,13,16,19-acid). Another important omega-3 PUFA is eicosapentaenoic acid ("EPA") which is designated "20:5 n-3" (all-cis-5,8,11,14,17-eicosapentaenoic acid). An important omega-6 PUFA is arachidonic acid ("ARA") which is designated "20:4 n-6" (all-cis-5,8,11,14-eicosatetraenoic acid).

Other omega-3 PUFAs include:
Eicosatrienoic acid (ETE)20:3 (n-3) (all-cis-11,14,17-eicosatrienoic acid). Eicosatetraenoic acid (ETA) 20:4 (n-3) (all-cis-8,11,14,17-eicosatetraenoic acid). Heneicosapentaenoic acid (HPA) 21:5 (n-3) (all-cis-6,9,12,15,18-heneicosapentaunoic acid); Docosapentaenoic acid (Clupancdcnic acid) (DPA) 22:5 (n-3) (all-cis-7,10,13,16,19-docosapentaonoic acid), Tetracosapentaerioic acid 24:5 (n-3) (all-cis-9,12,15,18,21-tetracosahexaerioic acid). Tetracosahexaerioic acid (Nisinic acid) 24:6 (n-3) (all-cis-6,9,12,15,18,21-tetracosahexaerioic acid).

Other omega-6 PUFAs include:
Eicosadienoic acid 20:2 (n-6) (all-cis-11,14-eicosadienoic acid). Dihorno-gamma-linolenic acid (DGLA) 20:3 (n-6) (all-cis-3,11,14-eicosatrienoic acid), Docosadienoic acid 22:2 (n-6) (all-cis-13,16-docosadienoic acid), Adrenic acid 22:4 (n-6)(all-cis-7,10,13,16-docosatetraenoic acid). Docosapentaenoic acid (Osbond acid) 22:5 (n-6) (all-cis-4,7,10,13,16-docosapentaenoic acid), Tetracosapentaenoic acid 24:4 (n-6) (all-cis-9,12,15,18-tetracosatetraenoic acid), Tetracosapentaenoic acid 24:5 (n-6) (all-cis-6,9,12,15,18-tetracosapentaenoic acid).

Preferred omega-3 PUFAs used in the embodiments of the present invention are docosahoxaenoic acid ("DHA") and eicosapentaenoic acid ("EPA").

Without wanting to be bound by theory it appears that the increased stability towards oxidation achieved by the process of the present invention is a result of salt formation between lysine and PUFA. Corresponding stability increase is not observed for PUFAs that remain free acids, or form part of an ester or an inorganic salt, e.g. with Na+, K+, Ca2+, or Mg2+.

Compositions comprising polyunsaturated omega-3 fatty acids that can be stabilized against oxidation by the process of the present invention may be any compositions containing substantial amounts of free polyunsaturated omega-3 fatty acids. Such compositions may further comprise other naturally occurring fatty acids in free form. In addition, such compositions may further comprise constituents that by themselves are solid, liquid or gaseous at room temperature and standard atmospheric pressure. Corresponding liquid constituents include constituents that can easily be removed by evaporation and could thus be considered as volatile constituents as well as constituents that are difficult to remove by evaporation and could thus be considered as non-volatile constituents. In the present context gaseous constituents are considered as volatile constituents. Typical volatile constituents are water, alcohols and supercritical carbon dioxide.

Compositions comprising polyunsaturated omega-3 fatty acids that can be stabilized against oxidation by the process of the present invention may be obtained from any suitable source material which, additionally, may have been processed by any suitable method of processing such source material. Typical source materials include any part of fish carcass, vegetables and other plants as well as material derived from microbial and/or algal fermentation. Typically such material, further, contains substantial amounts of other naturally occurring fatty acids. Typical methods of processing such source materials may include steps for obtaining crude oils such as extraction and separation of the source material, as well as steps for refining crude oils such as settling and degumming, deodorization, bleaching and deodorization, and further steps for producing omega-3 PUFA-concentrates from refined oils such as de-acidification, trans-ester concentration, and deodorization (cf. e.g. EFSA Scientific Opinion on Fish oil for Human Consumption) Any processing of source materials may further include steps for at least partially transforming omega-3 PUFA-esters into the corresponding free omega-3 PUFAs or inorganic salts thereof.

Preferred compositions composing polyunsaturated omega-3 fatty acids that can be stabilized against oxidation by the process of the present invention can be obtained from compositions mainly consisting of esters of omega-3 PUFAs and other naturally occurring fatty acids by cleavage of the ester bonds and subsequent removal of the alcohols previously bound as esters. Preferably, ester cleavage is performed under basic conditions. Methods for ester cleavage are well known in the art.

In the context of the present invention stabilizing compositions against oxidation means that the stability of such compositions towards oxidation is increased. One measure for quantifying the stability of a composition towards oxidation is the induction time in a Rancimat test. Protocols for performing the Rancimat test are well known in the art and/or provided by manufacturers of instruments used for performing the Rancimat test. An alternative measure for the stability of a composition towards oxidation can be obtained as follows. The stability of two or more samples of any composition or compound towards oxidation can be compared by (1) initially measuring the degree of oxidation of the samples, followed by (2) subjecting the samples to comparable (oxidizing) conditions and (3) measuring the degree of oxidation of the samples thereafter. The sample with the smallest increase of its degree of oxidation exhibits the highest stability towards oxidation under the given conditions, whereas the sample with the largest increase of its degree of oxidation exhibits the lowest stability towards oxidation under the given conditions increase of the degree of oxidation of a sample can be expressed in absolute terms, i.e as the difference of the values obtained before and after subjecting to oxidizing conditions, or, alternatively, the increase can be expressed in relative terms, i.e. as the ratio of the values obtained before and after subjecting to oxidizing conditions. Evidently, a decrease of the degree of oxidation resulting from exposure to oxidizing conditions indicates a very high level of stability towards oxidation which should be interpreted as being even higher than the level of stability of a sample yielding an unchanged degree of oxidation as a result of exposing the sample to comparable oxidizing conditions.

Several measures are known in the art for quantifying the degree of oxidation of a sample. In the broadest sense of the present invention, any of these measures can be used. In preferred embodiments of the present invention one or more of the following measures are used for quantifying the degree of oxidation: Peroxide Value (PV), Anisidine Value (AV), Totox Value. PV is a measure of primary oxidation products (hydroperoxide-formation at double bonds) and AV is a measure of secondary degradation products (carbonyl compounds). Totox Value is calculated as Totox=2*PV+AV (wherein PV is specified in milliequivalents $O_2$ per kg of sample). Procedures for determining Peroxide Value (PV) and Anisidine Value (AV) have bean described in the literature (cf. e.g. Official Methods and Recommended Practices of the AOCS, $6^{th}$ Edition 2013. Edited by David Firestone, ISBN 973-1-893997-74-5; or e g. PV can be determined according to Ph. Eur 2.5.5 (01/2008:20505). AV can be determined according to Ph. Eur 2.5.36 (01/2008:20536)).

An exemplary procedure for determining the Peroxide Value (PV) of a sample is performed as follows:

Reagents and solution:

1. Acetic Acid—chloroform solution (7.2 ml Acetic Acid and 4.8 ml Chloroform).
2. Saturated Potassium Iodide solution. Store in the dark.
3. Sodium thiosulfate solution, 0.1N. Commercially available
4. 1% Starch solution. Commercially available.
5. Distilled or deionized water.

Procedure:

Conduct a blank determination of the reagents

1. Weigh 2.00 (±0.02) g of sample into a 100 ml glass stoppered Erlenmeyer flask. Record weight to the nearest 0.01 g.
2. By graduated cylinder, odd 12 ml of the acetic acid chloroform solution.
3. Swirl the flask until the sample is completely dissolved (careful warming on a hot plate may be necessary).
4. Using 1 ml Mohr pipette, add 0.2 ml of saturated potassium iodide solution
5. Stopper the flask and swirl the contents of the flask for exactly one minute.
6. Immediately add by graduated cylinder, 12 ml of either distilled or deionized water, stopper and stake vigorously to liberate the iodine from the chloroform layer.
7. Fill the burette with 0.1 N sodium thiosulfate.
8. If the starting color of the solution is deep red orange, titrate slowly with mixing until the color lightens. If the solution is initially a light amber color, go to step 9.
9. Using a dispensing device: add 1 ml of starch solution as indicator.
10. Titrate until the blue gray color disappears in the aqueous (upper layer).
11. Accurately record the mis of titrant used to two decimal places.

Calculation:
S=titration of sample
B=titration of blank
Peroxide value=(S−B)*N thiosulfate*1000/weight of sample An exemplary procedure for determining the Anisidine Value (AV) of a sample is performed as follows The anisidine value is defined as 100 times the optical density measured in a 1 cm cell of a solution containing 1 g of the substance to be examined in 100 ml of a mixture of solvents and reagents according to the following method carry out the operations as rapidly as possible avoiding exposure to actinic light.

Test solution (a); Dissolve 0.500 g of the substance to be examined in trimethylpentane and dilute to 25.0 ml with the same solvent.

Test solution (b): To 5.0 ml of test solution (a) add 1.0 ml of a 2.5 g/t solution of p-anisidine in glacial acetic acid, shake and store protected from light.

Reference solution: To 5.0 ml of trimethylpentane add 1.0 ml of a 2.5 g/l solution of p-anisidine in glacial acetic acid, shake and store protected from light. Measure the absorbance of test solution (a) at the maximum at 350 nm using trimethylpentane as the compensation liquid. Measure the absorbance of test solution (b) at 350 nm exactly 10 min after its preparation, using the reference solution as the compensation liquid. Calculate the anisidine value (AV) from the expression.

$$AV=(25*(1.2*A1-A2)/m$$

A1=absorbance of test solution (b) at 350 nm,
A2=absorbance of test solution (a) at 350 nm,
m=mass of the substance to be examined in test solution (a), in grams.

When comparing the stability of samples towards oxidation by (1) measuring the degree of oxidation, (2) subjecting to oxidizing conditions, and (3) measuring the degree of oxidation again in the context of the present invention, preferably the degree of oxidation in steps (1) and (3) is assessed by determining Peroxide Value (PV) and/or Anisidine Value (AV); further, preferably, the oxidizing conditions in step (2) are selected from one of the following: storage in open containers exposed to air at room temperature over a defined period of time of at least ten days; storage in open containers exposed to air at 50° C. over a defined period of time of at least three days.

In the context of the present invention increasing the stability of a composition towards oxidation by a process means that at least one measure describing the stability of a composition towards oxidation, e.g. at least one measure as described above, is increased after the composition is subjected to the process.

In the context of the present invention starting compositions comprising at least one polyunsaturated omega-3 fatty acid component may be any compositions containing substantial amounts of at feast one polyunsaturated omega-3 fatty acid component wherein each type (i.e. molecular species) of free omega-3 PUFA (with "free" indicating the presence of a free carboxylic acid function) constitutes a different polyunsaturated omega-3 fatty acid component. Such compositions may further comprise other naturally occurring fatty acids in tree form. In addition, such compositions may further comprise constituents that by themselves are solid, liquid or gaseous at room temperature and standard atmospheric pressure. Corresponding liquid constituents include constituents that can easily be removed by evaporation and could thus be considered as volatile constituents as well as constituents that are difficult to remove by evaporation and could thus be considered as non-volatile constituents. In the present context gaseous constituents are considered as volatile constituents. Typical volatile constituents are water, alcohols and supercritical carbon dioxide.

Accordingly, typical starting compositions, without taking account for volatile constituents, have a PUFA-content PC (i.e. the total content of one or more free polyunsaturated omega-3 fatty acids) of at least 25 wt %, up to 75 wt % of other naturally occurring fatty acids in free form, and up to 5 wt % of other constituents that by themselves are solid or liquid at room temperature and standard atmosphere pressure. However, higher grades of polyunsaturated omega-3 fatty acids can be obtained by purification of the respective starting materials. In a preferred embodiment of the present invention starting compositions, without taking account for volatile constituents, have a PUFA-content PC (i.e. the total content of one or more free polyunsaturated omega-3 fatty acids) of at least 50 wt %, up to 50 wt % of other naturally occurring fatty acids in free form, and up to 5 wt % of other constituents that by themselves are solid or liquid at room temperature and standard atmospheric pressure. In another preferred embodiment of the present invention starting compositions, without taking account for volatile constituents, have a PUFA-content PC (i.e. the total content of one or more free polyunsaturated omega-3 fatty acids) of at toast 75 wt %, up to 25 wt % of other naturally occurring fatty acids in free form, and up to 5 wt % of other constituents that by themselves are solid or liquid at room temperature and standard atmospheric pressure. In another preferred embodiment of the present invention starting compositions, without taking account for volatile constituents, have a PUFA-content PC (i.e. the total content of one or more free polyunsaturated omega-3 fatty acids) of at least 90 wt %, up to 10 wt % of other naturally occurring fatty acids in free form, and up to 5 wt % of other constituents that by themselves are solid or liquid at room temperature and standard atmospheric pressure. In another preferred embodiment of the present invention starting compositions, without taking account for volatile constituents, have a PUFA-content PC (i.e the total content or one or more free polyunsaturated omega-3 fatty acids) of at least 90 wt %, up to 10 wt % of other naturally occurring fatty acids in free form, and up to 1 wt % of other constituents that by themselves are solid or liquid at room temperature and standard atmospheric pressure.

The lysine composition provided in step (ii) of the process of the present invention is a composition comprising substantial amounts of free Lysine (Lys). The lysine composition may further comprise constituents that by themselves are solid, liquid or gaseous at room temperature and standard atmospheric pressure. Corresponding liquid constituents include constituents that can easily be removed by evaporation and could thus be considered as volatile constituents as well as constituents that are difficult to remove by evaporation and could thus be considered as non-volatile constituents. In the present context gaseous constituents are considered as volatile constituents. Typical volatile constituents are water, alcohols and supercritical carbon dioxide. Typical lysine compositions contain at least 95 wt %, 97 wt %, 95 wt %, or 99 wt % of tree lysine, without taking account for volatile constituents. Preferred lysine compositions contain at least 98 wt % of free lysine, without taking account for volatile constituents.

In preferred embodiments of the present invention without accounting for volatile constituents, starting compositions contain mostly free PUFAs and other naturally occurring fatty acids in free form and lysine compositions contain mostly free lysine, thus yielding product compositions mostly consisting of salts of lysine with PUFAs and other naturally occurring fatty acids. Accordingly, in preferred embodiments of the present invention, starting composition in step (i) and lysine composition in step (ii) are provided in such a manner that at least sp wt % of the product composition consist of one or more salts of cations derived from lysine with anions derived from one or more polyunsaturated omega-3 fatty acids and other naturally occurring fatty acids, wherein sp is selected from 90, 95, 97, 98, 99, 100.

In step (iii) of the process of the present invention starting composition and lysine composition are combined. Combining can be achieved by any means allowing formation of a product composition comprising at least one salt of a cation derived from lysine with an anion derived from a polyunsaturated omega-3 fatty acid. Accordingly, a typical way of combining starting composition and lysine composition would be admixing aqueous, aqueous-alcoholic or alcoholic solutions of each and removing the solvent subsequently. Alternatively, depending on the remaining constituents of starting composition and lysine composition, it may not be necessary to add solvents but could be sufficient to combine starting composition and lysine composition directly. In the context of the present invention a preferred way of combining starting composition and lysine composition is admixing aqueous, aqueous-alcoholic or alcoholic solutions of each and removing the solvent subsequently.

In the context of the present invention a cation derived from lysine is a cation obtained by protonation of lysine.

In the context of the present invention an anion derived from a polyunsaturated omega-3 fatty acid is an anion obtained by deprotonation of a polyunsaturated omega-3 fatty acid.

It should be noted that salts of lysine with polyunsaturated fatty acids per se were known in the art (cf. EP 0734373 B1), however, it was unknown that such salts exhibit higher stability towards oxidative degradation as compared to free PUFAs or PUFA-esters.

In view of the intrinsic stability of salts of lysine with omega-3 PUFAs it is unnecessary to add substantial amounts of antioxidants to these salts. Accordingly, in preferred embodiments of the present invention the product composition obtained in step (iii) contains no substantial amounts of antioxidants, wherein no substantial amounts means that this composition contains less than 5 wt %, 3 wt %, 1 wt %, or 0.1 wt % of antioxidants. In further preferred embodiments the product composition contains no antioxidants at all. In preferred embodiments of toe present invention the product composition contains no substantial amounts of antioxidants, wherein no substantial amounts means that the product composition contains less than 5 wt %, 3 wt %, 1 wt %, or 0.1 wt % of antioxidants and wherein the antioxidants are salaried from vitamin C and asters thereof, erythorbic acid and esters thereof, vitamin E and esters thereof, polyphenols and esters thereof carotinoids, gallates and esters thereof, butylated hydroxyanisole and esters thereof, butylated hydroxytoluene and esters thereof, rosemary oil, hexylresorcinol and esters thereof. In further preferred embodiments the product composition contains no antioxidants at all, wherein the antioxidants are selected from vitamin C and esters thereof, erythorbic acid and esters thereof vitamin E and esters thereof, polyphenols end esters thereof, carotinoids gallates and esters thereof, butylated hydroxyanisole and esters thereof, butylated hydroxytuone and esters thereof, rosemary oil, hexylresorcinol and esters thereof.

According to the invention toe product composition exhibits higher stability towards oxidation than the starting composition. This means that at least one measure describing the stability of a composition towards oxidation, e.g. at least one measure as described above, indicates a higher stability towards oxidation for the product composition than for the starting composition.

In preferred embodiments of the present invention free carboxylic acid functions and lysine are provided in roughly equimolar quantities in order to facilitate quantitative salt formation. Accordingly, in a preferred embodiment in the process of the present invention lysine composition in step (ii) is provided in such a manner that the ratio R=n(ca)/n(lys) of the amount of carboxylic acid functions n(ca) in the starting composition provided in step (i) and the total amount of free lysine n(lys) in the lysine composition provided in step (ii) is in a range selected from 0.9<R<1.1, 0.95<R<1.05, 0.98<R<1.02. In a particularly preferred embodiment R is in the range 0.98<R<1.02. The amount of carboxylic acid functions n(ca) in the starting composition provided in step (i) can be determined by standard analytical procedures well known in the art. e.g. acid base titration.

In preferred embodiments of the present invention lire starting composition provided in step (i), does not contain substantial amounts of fatty acid esters, thus yielding a product composition devoid of substantial amounts of fatty add esters as well. Accordingly, in preferred embodiments of the present invention the starting composition provided in step (i) does not contain more than x(fe) wt % of fatty acid esters, thus yielding a product composition comprising a maximum of x(fe) wt % of fatty acid esters, wherein x(fe) is selected from 5, 3, 1, 0.3, 0. In particularly preferred embodiments x(fe) is 1.

As noted above, salts of lysine with polyunsaturated fatty acids per se were known in the art (cf. EP 0734373 B1) however, it was unknown that such salts exhibit higher stability towards oxidative degradation as compared to free PUFAs or PUFA-esters. Importantly, further, lysine-PUFA salts were described as "very thick transparent oils, which transform into solids of waxy appearance and consistency at low temperatures" (cf. EP 0734373 B1, page 1, lines 47 to 48). As a result, a person of skill in the art could not have expected that salts of lysine with omega-3 PUFAs could be obtained via spray drying procedures. Instead, a person of skill would have expected that such salts would (a) deteriorate under spray drying conditions due to oxidative damage under elevated temperatures in the absence of substantial amounts of solvents, antioxidants and protective coatings, and (b) agglomerate into dumps mechanically prohibitive to the process of spray drying in view of the presumed appearance of such salts as waxy solids. It is therefore remarkable that, presently, it was found that salts of lysine with omega-3 PUFAs can in fact be obtained via spray drying in a facile manner. Conditions for spray drying, always, have to be adapted to the particular spray-drying equipment used. However, it is well within the scope of routine laboratory work of a person of skill in the art to perform such adaption in the present erase.

In order to perform the spray drying step according to the process of the present invention aqueous, aqueous-alcoholic or alcoholic solutions are used. It was found that Lys-salts of PUFAs dissolve poorly in neat alcoholic solvents. It was, further, found that such salts exhibit gel like appearance when dissolved at high concentration in neat water. Aqueous-alcoholic solvent systems may thus be employed for avoiding such problems. Accordingly, in preferred embodiments of the present invention the solvent of the admixture subjected to spray drying conditions is an aqueous-alcoholic solvent system containing 20 wt % to 90 wt % water and 80 wt % to 10 wt % alcoholic solvents.

The solvents content of the solid product composition will vary depending on spray drying conditions and substrates used, however, it was presently found that even at very low solvent contents in the solid product composition oxidative damage does not occur. As outlined further above, this could not have been expected. Preferably, thus, according to the present invention a solid product composition with a low solvent content is obtained. Thus, according to the present invention in step (iii) aqueous, aqueous-alcoholic or alcoholic solutions of starting composition and lysine composition are first admixed, and subjected to spray drying conditions subsequently, thus yielding a solid product composition comprising at least one salt of a cation derived from lysine with an anion derived from a polyunsaturated omega-3 fatty acid, with a solvent content SC selected from the following: SC<5 wt %, SC<3 wt %, SC<1 wt %, SC<0.5 wt %. In a particularly preferred embodiment of the present invention SC is selected as SC<1 wt %.

The present invention, further, comprises compositions obtainable by any of the processes of the invention.

The present invention, further, comprises use of compositions, obtainable by any of the processes of the invention, for the manufacture of food products comprising polyunsaturated omega-3 fatty acids.

In the context of the present invention food products comprise but are not limited to baked goods, vitamin supplements, diet supplements, powdered drinks, doughs, batters, baked food items including e.g. cakes, cheesecakes, pies, cupcakes, cookies, bars, breads, rolls, biscuits, muffins, pastries, scones, and croutons; liquid food products e.g. beverages, energy drinks, infant formula, liquid meals, fruit juices, multivitamin syrups, meal replacers, medicinal foods, and syrups; semi-solid food products such as baby food, yogurt, cheese, cereal, pancake mixes; food bars including energy bars; processed meals; ice creams; frozen desserts; frozen yogurts; waffles mixes; salad dressings; and replacement egg mixes; and further cookies, crackers, sweet goods, snacks, pies, granola/snack bars, and toaster pastries; salted snacks such as potato chips, corn chips, tortilla chips, extruded snacks, popcorn, pretzels, potato crisp, and nuts; specialty snacks such as dips, snacks such as candy; instant food products, such as instant noodles, instant soup cubes or granulates.

The present invention, further, comprises use of compositions obtainable by any of the processes of the invention, for the manufacture of nutritional products comprising polyunsaturated omega-3 fatty acids.

In the context of the present invention nutritional products comprise any type of nutraceutical nutrient or dietary supplement, e.g. for supplementing vitamins, minerals, fiber, fatty acids, or amino acids.

The present invention, further, comprises use of compositions, obtainable by any of the processes of the invention, for the manufacture of pharmaceutical products comprising polyunsaturated omega-3 fatty acids.

In the context of the present invention the pharmaceutical product can further comprise a pharmaceutically acceptable excipient as well as further pharmaceutically active agents including for example cholesterol-lowering agents such as statins, anti-hypertensive agents, anti-diabetic agents, anti-dementia agents, anti-depressants, anti-obesity agents, appetite suppressants and agents to enhance memory and/or cognitive function.

Preferred processes of the present invention are characterized by one the following selections $0.90<R<1.10$, $x(fe)=5$; PC=25; SC<1 wt %
$0.90<R<1.10$, $x(fe)=3$; PC=25; SC<1 wt %
$0.90<R<1.10$, $x(fe)=2$; PC=25; SC<1 wt %
$0.90<R<1.10$, $x(fe)=1$; PC=25; SC<1 wt %
$0.95<R<1.05$, $x(fe)=5$; PC=25; SC<1 wt %
$0.95<R<1.05$, $x(fe)=3$; PC=25; SC<1 wt %
$0.95<R<1.05$, $x(fe)=2$; PC=25; SC<1 wt %
$0.95<R<1.05$, $x(fe)=1$; PC=25; SC<1 wt %
$0.98<R<1.02$, $x(fe)=5$; PC=25; SC<1 wt %
$0.98<R<1.02$, $x(fe)=3$; PC=25; SC<1 wt %
$0.98<R<1.02$, $x(fe)=2$; PC=25; SC<1 wt %
$0.98<R<1.02$, $x(fe)=1$; PC=25; SC<1 wt %
$0.90<R<1.10$, $x(fe)=5$; PC=50; SC<1 wt %
$0.90<R<1.10$, $x(fe)=3$; PC=50; SC<1 wt %
$0.90<R<1.10$, $x(fe)=2$; PC=50; SC<1 wt %
$0.90<R<1.10$, $x(fe)=1$; PC=50; SC<1 wt %
$0.95<R<1.05$, $x(fe)=5$; PC=50; SC<1 wt %
$0.95<R<1.05$, $x(fe)=3$; PC=50; SC<1 wt %
$0.95<R<1.05$, $x(fe)=2$; PC=50; SC<1 wt %
$0.95<R<1.05$, $x(fe)=1$; PC=50; SC<1 wt %
$0.98<R<1.02$, $x(fe)=5$; PC=50; SC<1 wt %
$0.98<R<1.02$, $x(fe)=3$; PC=50; SC<1 wt %
$0.98<R<1.02$, $x(fe)=2$; PC=50; SC<1 wt %
$0.98<R<1.02$, $x(fe)=1$; PC=50; SC<1 wt %
$0.90<R<1.10$, $x(fe)=5$; PC=75; SC<1 wt %
$0.90<R<1.10$, $x(fe)=3$; PC=75; SC<1 wt %
$0.90<R<1.10$, $x(fe)=2$; PC=75; SC<1 wt %
$0.90<R<1.10$, $x(fe)=1$; PC=75; SC<1 wt %
$0.95<R<1.05$, $x(fe)=5$; PC=75; SC<1 wt %
$0.95<R<1.05$, $x(fe)=3$; PC=75; SC<1 wt %
$0.95<R<1.05$, $x(fe)=2$; PC=75; SC<1 wt %
$0.95<R<1.05$, $x(fe)=1$; PC=75; SC<1 wt %
$0.98<R<1.02$, $x(fe)=5$; PC=75; SC<1 wt %
$0.98<R<1.02$, $x(fe)=3$; PC=75; SC<1 wt %
$0.98<R<1.02$, $x(fe)=2$; PC=75; SC<1 wt %
$0.98<R<1.02$, $x(fe)=1$; PC=75; SC<1 wt %
$0.90<R<1.10$, $x(fe)=5$; PC=90; SC<1 wt %
$0.90<R<1.10$, $x(fe)=3$; PC=90; SC<1 wt %
$0.90<R<1.10$, $x(fe)=2$; PC=90; SC<1 wt %
$0.90<R<1.10$, $x(fe)=1$; PC=90; SC<1 wt %
$0.95<R<1.05$, $x(fe)=5$; PC=90; SC<1 wt %
$0.95<R<1.05$, $x(fe)=3$; PC=90; SC<1 wt %
$0.95<R<1.05$, $x(fe)=2$; PC=90; SC<1 wt %
$0.95<R<1.05$, $x(fe)=1$; PC=90; SC<1 wt %
$0.98<R<1.02$, $x(fe)=5$; PC=90; SC<1 wt %
$0.98<R<1.02$, $x(fe)=3$; PC=90; SC<1 wt %
$0.98<R<1.02$, $x(fe)=2$; PC=90; SC<1 wt %
$0.98<R<1.02$, $x(fe)=1$; PC=90; SC<1 wt %

Preferred compositions obtainable by a process of the invention utilizing spray drying in step (iii) as disclosed in the specification are characterized by one the following selections:

$0.90<R<1.10$, $x(fe)=1$; SC<3 wt %, sp=90
$0.90<R<1.10$, $x(fe)=1$; SC<3 wt %, sp=95
$0.90<R<1.10$, $x(fe)=3$; SC<3 wt %, sp=90
$0.90<R<1.10$, $x(fe)=3$; SC<3 wt %, sp=95
$0.95<R<1.05$, $x(fe)=1$; SC<3 wt %, sp=90
$0.95<R<1.05$, $x(fe)=1$; SC<3 wt %, sp=95
$0.95<R<1.05$, $x(fe)=3$; SC<3 wt %, sp=90
$0.95<R<1.05$, $x(fe)=3$; SC<3 wt %, sp=95
$0.98<R<1.02$, $x(fe)=1$; SC<3 wt %, sp=95
$0.98<R<1.02$, $x(fe)=1$; SC<3 wt %, sp=97
$0.98<R<1.02$, $x(fe)=3$; SC<3 wt %, sp=95
$0.98<R<1.02$, $x(fe)=3$; SC<3 wt %, sp=97
$0.90<R<1.10$, $x(fe)=1$; SC<1 wt %, sp=90

0.90<R<1.10, x(fe)=1; SC<1 wt %, sp=95
0.90<R<1.10, x(fe)=3; SC<1 wt %, sp=90
0.90<R<1.10, x(fe)=3; SC<1 wt %, sp=95
0.95<R<1.05, x(fe)=1; SC<1 wt %, sp=90
0.95<R<1.05, x(fe)=1; SC<1 wt %, sp=95
0.95<R<1.05, x(fe)=3; SC<1 wt %, sp=90
0.95<R<1.05, x(fe)=3; SC<1 wt %, sp=90
0.98<R<1.02, x(fe)=1; SC<1 wt %, sp=95
0.98<R<1.02, x(fe)=1; SC<1 wt %, sp=97
0.98<R<1.02, x(fe)=3; SC<1 wt %, sp=95
0.98<R<1.02, x(fe)=3; SC<1 wt %, sp=97
0.90<R<1.10, x(fe)=1; SC<0.5 wt %, sp=90
0.90<R<1.10, x(fe)=1; SC<0.5 wt %, sp=95
0.90<R<1.10, x(fe)=3; SC<0.5 wt %, sp=90
0.90<R<1.10, x(fe)=3; SC<0.5 wt %, sp=95
0.95<R<1.05, x(fe)=1; SC<0.5 wt %, sp=90
0.95<R<1.05, x(fe)=1; SC<0.5 wt %, sp=95
0.95<R<1.05, x(fe)=3; SC<0.5 wt %, sp=90
0.95<R<1.05, x(fe)=3; SC<0.5 wt %, sp=95
0.98<R<1.02, x(fe)=1; SC<0.5 wt %, sp=95
0.98<R<1.02, x(fe)=1; SC<0.5 wt %, sp=97
0.98<R<1.02, x(fe)=3; SC<0.5 wt %, sp=95
0.98<R<1.02, x(fe)=3; SC<0.5 wt %, sp=97

EXPERIMENTS

Analytical Methods:

Primary oxidation products (hydroperoxides at double bonds) were quantified by determining the Peroxide Value (PV) according to Ph. Eur 2.5.5 (01/2008.20505). Secondary oxidation products (carbonyl compounds) were quantified by determining the Anisidine Value (AV) according to Ph, Eur. 2.5.36 (01/2008:20536).

Oligomeric PUFA constituents as well as their derivatives (collectively referred to as oligomer content) were quantified by gel-chromatographic means (GPC, styroldivinylbenzene-phase with tetrahydrofuran containing trifluoroacetic acid used as eluent). A refractive index (RI) detector was used for detection. Due to the fact that specific response factors of the constituents of the samples wore unknown, proportions were calculated based upon fractional proportions of the total area of chromatograms.

Water content was determined by Karl-Fischer titration.

Ethanol content was determined by 1-H-NMR spectroscopy.

Acid values were determined by titration with potassium hydroxide.

Experiment 1: Eicosapentaenoic Acid (EPA) from Eicosapentaenoic Acid Ethyl Ester (EPA-OEt)

5.00 kg of (commercially available, standard quality) eicosapeotaenoic acid ethyl ester (EPA-OEt) with calculated EPA-content of 92.0% (92.0 wt % free EPA of total weight), an Anisidine Value of 5.0 A/g, a Peroxide Value of 6.5 mmol/kg and an oligomer content of 0.2 area-% (gel-chromatography, RI-detector) was placed in a 30 L double jacket vessel (rendered inert with nitrogen) and diluted with 5.0 L ethanol. 1.6 kg of NaOH (50%) solution was added and the resulting solution stirred for 30 min at 30° C.-50° C. Subsequently, the reaction mixture was diluted with 15 L of water and 1.4 L of phosphoric acid (85%) was added thereafter. Phases were separated after 10 min of subsequent stirring and the product phase was washed with 5 L of water. 4.639 kg oicosapentaonoic acid was obtained as an oil with an Anisidine Value of 3.1 A/g and a Peroxide Value of 8.6 mmol/kg. Oligomer content was not determined.

Experiment 2: Docosahexaenoic Acid (DHA) from Docoshexaenoic Acid Ethyl Ester (pHA-QEt)

5.00 kg of docosahexaenoic acid ethyl ester (commercially available, standard quality) with a calculated DHA content of 82.8% (82.8 wt % free DHA of total weight) and a total omaga-3 PUFA content of 92.8% (92.8 wt % free omega-3 PUFAs of total weight), an Anisidine Value of 16.0 A/g, a Peroxide Value of 26.1 mmol/kg and an oligomer content of 0.4 area-% (gei-chromatography RI-detector) was placed in a 30 L double jacket vessel (rendered inert with nitrogen) and diluted with 5.0 L ethanol. 1.6 kg of NaOH (50%) solution was added and the resulting solution stirred for 30 mm at 30° C.-50° C. Subsequently, the reaction mixture was diluted with 15 L of water and 1.4 L of phosphoric acid (85%) was added thereafter. Phases were separated after 10 min of subsequent stirring and the product phase was v/ashed with 5 L of water. 4.622 kg docosahexaenoic acid was obtained as an oil with an Anisidine Value of 1.7 A/g and a Peroxide Value of 7.9 mmol/kg. Oligomer content was not determined.

Experiment 3: Eicosapentaenoic Acid-L-Lysine (EPA-Lys) from Eicosapentaenoic Acid (EPA) and L-Lysine (L-Lys)

2.00 kg of eicosapentaenoic acid from experiment 1, exhibiting an acid value of 177.8 mg KOH/g upon titration, was dissolved in 2 kg of ethanol and combined with 1.69 kg of an aqueous L-lysine solution (51.3 wt-%). The homogenous solution obtained was spray dried with a custom built spray drier equipped with a two-substance nozzle and a 300 mm×900 mm drying chamber with an inlet temperature of 170° C. and an outlet tempwature of 80° C. 1.798 kg of a beige powder with a water content of 0.24% and an ethanol content of <0.1% were obtained. The salt exhibited an Anisidine Value of 2.1 A/g and a Peroxide Value of 1.3 mmol/kg. Oligomer content was not determined.

Experiment 4: Docosahexaenoic Acid-L-Lysine Salt (DHA-Lys) from Docoshexaenoic Acid (DHA) am L-Lysine (L-Lys)

2.00 kg of docosahexaenoic acid from experiment 2, exhibiting an acid value of 166.3 mg KOH/g upon titration, was dissolved in 2.0 kg of ethanol and combined with 1.81 kg of an aqueous L-lysine solution (51.3 wt-%). The homogenous solution obtained was spray dried with a custom built spray drier equipped with a two-substance nozzle and a 300 mm×900 mm drying chamber with an inlet temperature of 170° C. and an outlet temperature of 80° C. 1.892 kg of a beige powder with a water content of 0.27% and an ethanol content cf <0.1% were obtained. The salt exhibited an Anisidine Value of 3.1 A/g and a Peroxide Value of 1.7 mmol/kg. Oligomer content was not determined and NaOH Experiment 5: Eicosapentaenoic Acid-Sodium Salt (EPA-Na) from Eicosapentaenoic Acid (EPA) and NaOH 50 g of eicosapontaenoic acid obtained analogously to experiment 1, exhibiting an acid value of 183.3 mg KOH/g upon titration, was dissolved in 50 ml of ethanol and combined under stirring with 6.54 g sodium hydroxide in 30 ml of water. The homogenous solution obtained was spray dried with a Büchi B190 laboratory-spray drier with an inlet temperature of 140° C. and an outlet temperature of about 80° C. 28.6 g of a faintly beige powder were obtained. After storage for 3 months at room temperature the salt had obtained grey-coloured appearance and at that point exhibited an Anistdine Value of 41.1 A/g and a Peroxkle Value of 5.0 mmol/kg oligomer content was determined as 2.4 area-% (get-chromatography. RI-detector).

Experiment 6: Docosahexaenoic Acid-Sodium Salt (DHA-Na) from Docosahexaenoic Acid (DHA) and NaOh 50 g of docosahexaenoic acid obtained analogously to experiment 2, exhibiting an acid value of 169.5 mg KOH/g upon titration, was dissolved in 50 ml of ethanol and combined under stirring with 6.04 g sodium hydroxide in 30 ml of water. The homogenous solution obtained was spray dried with a Büchi B190 laboratory-spray drier writ an inlet temperature of 140° C. and an outlet temperature of about 80° C. 27.5 g of a faintly beige powder were obtained. After storage for 3 months at room temperature the salt had obtained grey-coloured appearance and at that point exhibited an Anisidine Value of 77.9 A/g and a Peroxide Value of 6.9 mmol/kg. Oligomer content was determined as 3.4 area-% (gel-chromatography. RI-detector).

Experiment 7: Examination of Stability of PUFAs and Derivatives Thereof as to the Storage at Elevated Temperature (50° C.) and Exposure to Air About 50 g each of the liquid ethyl esters EPA-OEt and DHA-OEt used in experiments 1 and 2 as well as of the liquid fatty acids EPA and DHA obtained in experiments 1 and 2 were filled into 250 ml Schott Duran bottles with an inner diameter of about 60 mm (filling height about 20 mm). About 50 g each of the solid lysine-salts EPA-Lys and DHA-Lys obtained in experiments 3 and 4 were filled into 250 ml polyethylene wide-neck bottles (55 mm*55 mm*80 mm) (filling height about 60 mm-70 mm).

All of the bottles were placed together with opened lids in a drying oven with an opened ventilation valve at 50° C. and stored under these conditions for 26 days. Results of the analyses performed subsequently as well as the results obtained for the sodium-salts which were stored at room temperature (cf. experiments 5 and 6) are summarized in the following table (Table 1).

The invention claimed is:

1. A solid product composition, comprising:
   at least one salt of a cation derived from lysine with an anion derived from a polyunsaturated omega-3 fatty acid, said solid product composition formed by:
   admixing an aqueous, an aqueous-alcoholic or an alcoholic solution of a starting composition comprising at least one polyunsaturated omega-3 fatty acid component and a lysine composition, and subjecting a resulting admixture to spray drying conditions subsequently, thus forming the solid product composition comprising at least one salt of a cation derived from lysine with an anion derived from a polyunsaturated omega-3 fatty acid;
   wherein the solid product composition has a solvent content of less than 5 wt %, and
   wherein at least 90 wt % of the solid product composition consists of one or more salts of cations derived from lysine with anions derived from one or more polyunsaturated omega-3 fatty acids and other fatty acids.

2. The solid product composition according to claim 1, wherein said starting composition is a food product comprising the polyunsaturated omega-3 fatty acid.

3. The solid product composition according to claim 1, wherein said starting composition is a nutritional product comprising the polyunsaturated omega-3 fatty acid.

4. The solid product composition according to claim 1, wherein said starting composition is a pharmaceutical product comprising the polyunsaturated omega-3 fatty acid.

5. The solid product composition according to claim 1, wherein the solid product composition has a solvent content of less than 3 wt %.

6. The solid product composition according to claim 1, wherein the lysine composition has a ratio R=n(ca)/n(lys) of the amount of carboxylic acid functions n(ca) in the starting composition and the amount of lysine n(lys) in the lysine composition is in a range of 0.95<R<1.05.

7. The solid product composition according to claim 1, wherein the starting composition does not contain more than 3 wt % fatty acid esters.

8. The solid product composition according to claim 1, wherein at least 97 wt % of the product composition consists of one or more salts of cations derived from lysine with anions derived from one or more polyunsaturated omega-3 fatty acids and other naturally occurring fatty acids.

9. The solid product composition according to claim 1, wherein an increased stability towards oxidation of the solid product composition does not comprise microencapsulation.

TABLE 1

|  |  | Anisidine Value (AV) [A/g] | | Peroxide Value (PV) [mmol/kg] | | Oligomer content [area-%]* | |
|---|---|---|---|---|---|---|---|
|  | Experiment | t = 0 | t = 26 days | t = 0 | t = 26 days | t = 0 | t = 26 days |
| EPA-OEt | 1 - starting material | 5.0 | 1843 | 6.5 | 267.7 | 0.2 | 37.0 |
| DHA-OEt | 2 - starting material | 16.0 | 1732 | 26.1 | 282.0 | 0.4 | 32.6 |
| EPA-OH | 1 | 3.1 | 424 | 8.6 | 14.7 | n.d. | 20.6 |
| DHA-OH | 2 | 1.7 | 894 | 7.9 | 20.6 | n.d. | 34.7 |
| EPA-Lys | 3 | 2.1 | <1.0 | 1.3 | <1.0 | n.d. | 0.6 |
| DHA-Lys | 4 | 3.1 | <1.0 | 1.7 | <1.0 | n.d. | 0.9 |
| EPA-Na | 5 | n.d. | 41.1 ** | n.d. | 5.0 ** | n.d. | 2.4 ** |
| DHA-Na | 6 | n.d. | 77.9 ** | n.d. | 6.9 ** | n.d. | 3.4 ** |

* gel-chromatography, RI-detector
** after 3 months at room temperature
n.d. = not determined 10. The solid product composition according to claim 1, wherein the solid product composition is free of antioxidants or contains less than 5 wt % of antioxidants.

11. The solid product composition according to claim 1, wherein the at least one polyunsaturated omega-3 fatty acid component comprises eicosapentaenoic acid (EPA).

12. The solid product composition according to claim 11, wherein the lysine comprises free lysine.

13. The solid product composition according to claim 1, wherein the solid product composition has a solvent content of less than 0.5 wt %.

14. The solid product composition according to claim 1, wherein the solid product composition contains no antioxidants.

15. The solid product composition according to claim 1, wherein the solid product composition has a solvent content of less than 1 wt %.

16. The solid product composition according to claim 1, wherein the at least one polyunsaturated omega-3 fatty acid component comprises docosahexaenoic acid (DHA).

17. A spray-dried solid product composition according to claim 1, has an increased stability towards oxidation, and does not include microencapsulation or antioxidants, and wherein the composition contains at most 1 wt % of fatty acid esters.

18. The solid product composition according to claim 1, wherein the lysine composition has a ratio $R=n(ca)/n(lys)$ of the amount of carboxylic acid functions $n(ca)$ in the starting composition and the amount of lysine $n(lys)$ in the lysine composition in a range selected from $0.9<R<1.1$, $0.95<R<1.05$, or $0.98<R<1.02$.

19. The solid product composition according to claim 1, wherein the starting composition does not contain more than 5 wt % of fatty acid esters.

20. The solid product composition according to claim 1, wherein at least 95 wt % of the solid product composition consists of one or more salts of cations derived from lysine with anions derived from one or more polyunsaturated omega-3 fatty acids.

* * * * *